(12) United States Patent
Voss et al.

(10) Patent No.: US 8,715,303 B2
(45) Date of Patent: May 6, 2014

(54) SIZING AND POSITIONING ADAPTER FOR MEDICAL INSTRUMENTS

(75) Inventors: Laveille Kao Voss, Belmont, CA (US); Erik Kristian Walberg, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 1688 days.

(21) Appl. No.: 10/861,171

(22) Filed: Jun. 4, 2004

(65) Prior Publication Data

US 2005/0021047 A1 Jan. 27, 2005

Related U.S. Application Data

(60) Provisional application No. 60/476,573, filed on Jun. 6, 2003, provisional application No. 60/502,316, filed on Sep. 12, 2003.

(51) Int. Cl.
*A61B 17/08* (2006.01)
(52) U.S. Cl.
USPC .......................................... 606/153; 606/151
(58) Field of Classification Search
USPC ........ 604/164.01, 164.11, 264; 606/185, 153; 600/104
See application file for complete search history.

(56) References Cited

U.S. PATENT DOCUMENTS

| | | | |
|---|---|---|---|
| 4,435,174 A * | 3/1984 | Redmond et al. | 604/174 |
| 4,449,532 A | 5/1984 | Storz | |
| 4,686,984 A | 8/1987 | Bonnet | |
| 4,862,891 A | 9/1989 | Smith | |
| 4,994,027 A | 2/1991 | Farrell | |
| 5,058,567 A * | 10/1991 | Takahashi et al. | 600/139 |
| 5,071,410 A | 12/1991 | Pazell | |
| 5,193,263 A * | 3/1993 | Takahashi | 29/447 |
| 6,080,102 A | 6/2000 | Konou et al. | |
| 6,117,144 A | 9/2000 | Nobles et al. | |
| 6,126,058 A * | 10/2000 | Adams et al. | 227/180.1 |
| 6,136,010 A | 10/2000 | Modesitt et al. | |
| 6,183,485 B1 | 2/2001 | Thomason | |
| 6,190,357 B1 * | 2/2001 | Ferrari et al. | 604/102.01 |
| 6,346,093 B1 * | 2/2002 | Allman et al. | 604/167.06 |
| 6,520,907 B1 | 2/2003 | Foley et al. | |
| 6,641,592 B1 | 11/2003 | Saur et al. | |
| 6,997,931 B2 * | 2/2006 | Sauer et al. | 606/139 |
| 2002/0107530 A1 | 8/2002 | Sauer et al. | |
| 2003/0045892 A1 | 3/2003 | Kaladelfos | |
| 2003/0073934 A1 | 4/2003 | Putz | |
| 2003/0233120 A1 | 12/2003 | Akerfeldt | |
| 2004/0225301 A1 | 11/2004 | Roop et al. | |

FOREIGN PATENT DOCUMENTS

| | | |
|---|---|---|
| EP | 1371333 | 12/2003 |
| GB | 2275420 | 8/1994 |
| WO | WO 2004/107990 | 1/2004 |

* cited by examiner

*Primary Examiner* — Corrine M McDermott
*Assistant Examiner* — Son Dang
(74) *Attorney, Agent, or Firm* — Workman Nydegger; Randy Shen

(57) ABSTRACT

In accordance with the present invention there is provided apparatuses and methods for using a medical instrument including a sizing and positioning adapter. The apparatus comprises an adapter for a medical instrument, the adapt having a body having a shim portion and an instrument holding portion adjacent the shim portion, wherein the shim portion provides an enlarged peripheral surface adjacent the medical instrument such that when the medical instrument is held in the instrument holding portion and the medical instrument and body are inserted through an opening in a patient tissue, at least a portion of the enlarged peripheral surface is in contact with at least a portion of the periphery of the opening in the patient tissue.

23 Claims, 17 Drawing Sheets

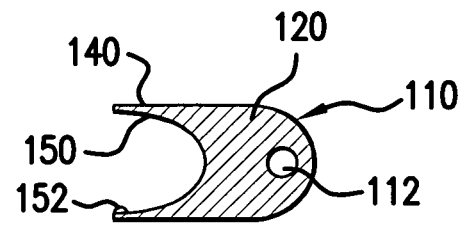
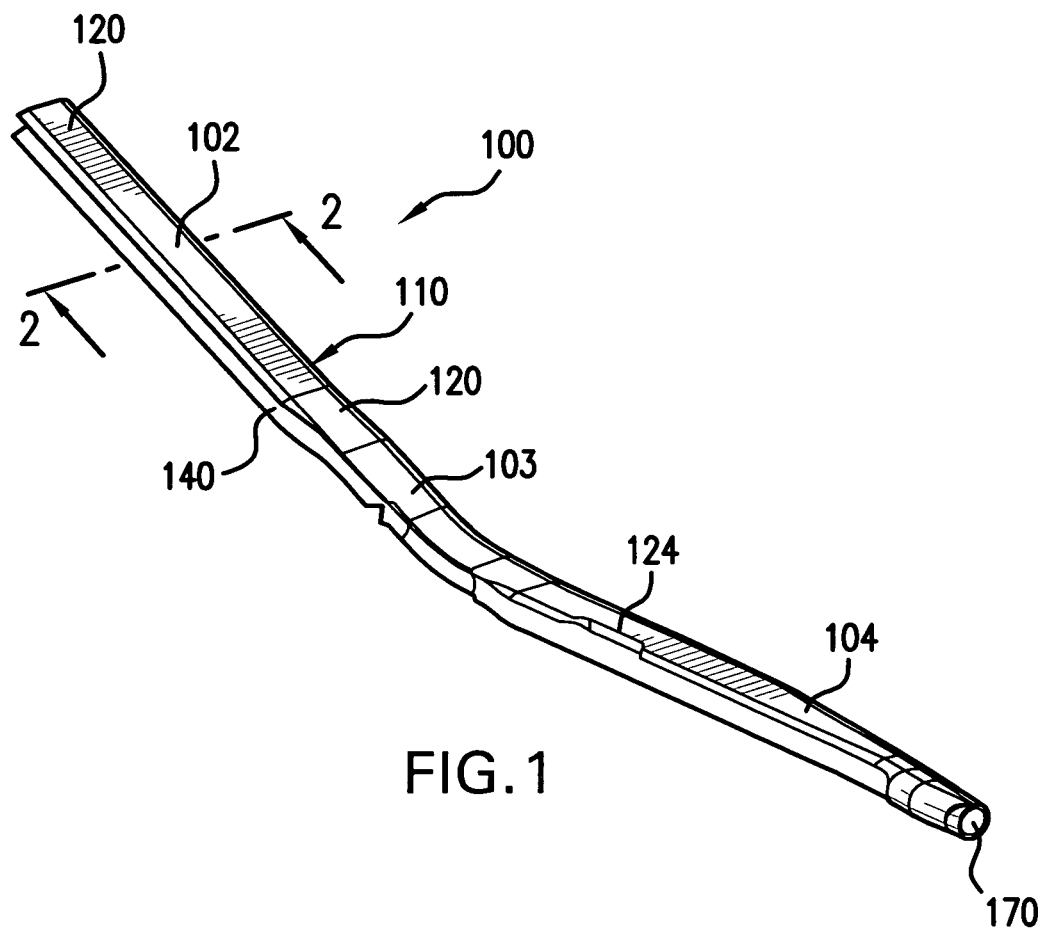

SIZING AND POSITIONING ADAPTER FOR MEDICAL INSTRUMENTS

PRIORITY CLAIM

The present application claims priority to the following U.S. Provisional Patent applications having Ser. Nos. 60/476,573 and 60/502,316 filed on Jun. 6, 2003 and Sep. 12, 2003 respectively, the entirety of which are hereby incorporated by reference.

FIELD OF THE INVENTION

The invention relates generally to medical instruments and, more particularly, to apparatus and methods for using a medical instrument including a sizing and positioning adapter.

BACKGROUND

A number of vascular diagnostic and interventional medical procedures are now performed translumenally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body, through a puncture in the femoral artery for example, and into the vascular lumen. Catheters or other medical devices are advanced into the patient's vasculature through the introducer sheath, and procedures such as balloon angioplasty, stent placement, etc. are performed.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudo-aneurysm formation, as well as arteriovenous fistula formation. These complications may require blood transfusion and/or surgical intervention.

The incidence of complications from compression induced hemostasis increases when the size of the introducer sheath grows larger, and/or when the patient is anti-coagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site.

A more effective approach for vascular closure has been proposed wherein a suture applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure. One such suturing device is described in U.S. Pat. No. 6,136,010, the full disclosure of which is incorporated herein by reference.

Other examples of devices that can be used to suture or otherwise close an opening in a patient tissue are described in U.S. Pat. Nos. 5,417,699 and 5,527,322 of Klein et al.; U.S. Pat. No. 5,902,311 of Andreas et al.; U.S. Pat. No. 6,245,079 of Nobles et al.; U.S. Pat. No. 6,436,109 of Kontos; U.S. Pat. No. 5,304,184 of Hathaway et al.; U.S. Pat. Nos. 5,431,666 and 5,562,686 of Sauer et al.; U.S. Pat. No. 5,676,689 to Kensey et al.; and U.S. Pat. No. 6,391,048 to Ginn et al., the full disclosures of which are incorporated herein by reference.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall.

The ease of deployment and efficacy of the procedure can further be enhanced by reducing the cross-section of that portion of the device which is inserted into the tissue tract and/or the vessel itself, which may also allow closure of the vessel in a relatively short amount of time without imposing excessive injury to the tissue tract or vessel. In some cases, however, a larger size device may be appropriately used when the puncture is larger, as in the case of percutaneous repair of an aortic aneurysm using a stent graft (also referred to as abdominal aortic aneurysm (AAA) repair). Readily available suturing devices, which are smaller in size, are typically not desirable for closing such larger sized vessel punctures because the shaft or sheath diameter of such suturing devices are too small to provide hemostasis or adequate tissue capture during the closure procedure. Also, in such procedures, it may be desirable to close the puncture with more than one suture loop, in which case adapters may be provided on suturing devices that help position each loop of suture in a desired position relative to the puncture, as well as provide hemostasis. Such adapters may be used in lieu of provided larger size suturing devices.

For the above reasons, it would be desirable to provide improved devices, systems, and methods for suturing vascular punctures. It would be particularly beneficial if these improved devices provided some or all of the benefits while overcoming one or more of the disadvantages discussed above.

SUMMARY OF THE INVENTION

The present invention provides an adapter for a medical instrument includes a body having a shim portion and an instrument holding portion adjacent the shim portion. The shim portion provides an enlarged peripheral surface adjacent the medical instrument such that when the medical instrument is held in the instrument holding portion and the medical instrument and body are inserted through an opening in a patient tissue, at least a portion of the enlarged peripheral surface is in contact with at least a portion of the periphery of the opening in the patient tissue.

It is further contemplated in accordance with the present invention a medical device or a plurality of medical devices having bodies shaped similar to the adapters described herein may be provided to place suture in different locations relative to an opening in a patient's tissue. Additionally, a removable distal sheath portion may be provided, wherein the distal sheath portion is utilize to maintain hemostasis during a procedure wherein the multiple medical devices are utilized to close a larger opening as will be described in greater detail below.

In accordance with the present invention there is provided an adapter for a medical instrument, the adapter including a body having a shim portion and an instrument holding portion adjacent the shim portion, wherein the shim portion provides an enlarged peripheral surface adjacent the medical instrument such that when the medical instrument is held in the instrument holding portion and the medical instrument and body are inserted through an opening in a patient tissue, at least a portion of the enlarged peripheral surface is in contact with at least a portion of the periphery of the opening in the patient tissue.

In accordance with the present invention there is provided a medical device including an elongated medical instrument; and a body having a shim portion and an instrument holding portion adjacent the shim portion, wherein the shim portion provides an enlarged peripheral surface adjacent the medical instrument, and wherein the instrument holding portion is shaped to hold a section of the medical instrument.

In accordance with the present invention there is provided an adapter for a medical instrument, the adapter including an elongated body; an instrument holding portion defined along at least a portion of the length of the elongated body; and a shim portion along at least a portion of the length of the elongated body, the shim portion extending away from the instrument holding portion.

In accordance with the present invention there is provided a method of closing an opening formed in tissue, the method including the steps of: (a) attaching a first adapter to a medical instrument; (b) inserting the adapter and medical instrument into an opening formed in the tissue; (c) deploying the medical instrument; (d) retracting the adapter and medical instrument from the opening in the tissue; and repeating A-D as necessary to close the opening in the tissue.

In accordance with an alternative embodiment of the present invention there is provided a medical device configured for delivering at least one suture element adjacent an opening formed in a patient's tissue, wherein the medical device includes an enlarged cross-sectional area, the enlarged cross sectional area configured to position the medical instrument within the opening in a desired and/or specific orientation.

BRIEF DESCRIPTION OF THE DRAWINGS

Referring now to the appended drawings, wherein like numerals are utilized to denote similar objects.

FIG. 1 is a perspective view of an exemplary embodiment of an adapter in accordance with the present invention.

FIG. 2 is an enlarged partial cross-sectional view of the adapter of FIG. 1, taken along line 2-2 of FIG. 1.

DETAILED DESCRIPTION

Figure 3C:
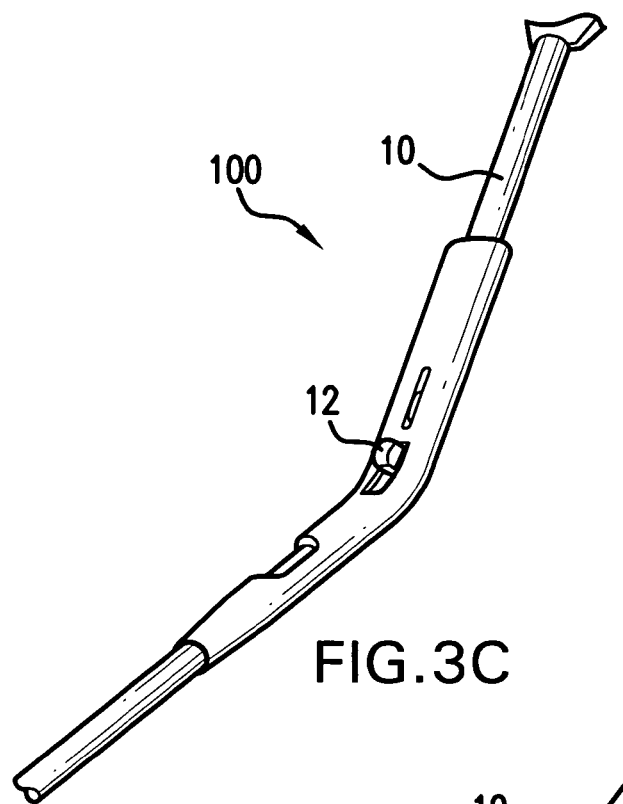
FIG. 3c is a perspective view of an adapter in accordance with the invention.

Various embodiments of an adapter described herein may be used with various medical instruments to change the effective circumference or size of a given medical instrument. Most suturing instruments that are used for closing vessel access punctures are available in limited ranges of sizes (such as 6 French to 10 French) that are applicable to most instances of percutaneous vessel access holes or punctures. In some instances, however, the vascular access puncture is much larger than the largest size instrument available. For example, AAA access holes can be up to 25 French. The adapter described herein can be provided for use with a 6 Fr. instrument, for example, to provide an instrument that is effectively larger for use in the closure of larger vascular access punctures. While smaller size suturing instruments can be adapted to close relatively larger sized holes in a technique known as "pre-closing," it is generally desirable to similarly match the instrument size to the size of the hole being closed. One purpose of matching the instrument size to the hole size is to provide hemostasis, i.e., to block the outflow of blood through the puncture, during the suturing procedure. Another purpose may be to manipulate the periphery of the puncture into an elongated, elliptical or other non-circular shape so that maximum tissue capture is achieved. For example, it is desirable for the needle punctures in the tissue through which the suture extends to be appropriately spaced from the periphery of the hole as possible to minimize the risk of suture tearing through tissue, while minimizing the overall diameter of the device.

Moreover, various embodiments of an adapter can be provided that hold the suturing instrument in a particular position with respect to the vessel puncture, so that multiple sutures can be placed at multiple locations across the puncture. As will be described in detail below, suture loops can be placed to the right, near the center, and to the left across the puncture with respect to the longitudinal direction of the vessel, for example.

Although the present invention is described and shown herein in used with a suture based medical instrument, it is contemplated that other medical instruments may be utilized with the adapter of the present invention. For example, the adapter of the present invention may be utilized with other technologies such as clips, glues, staples and the like.

In accordance with the present invention there is provided an adapter or a plurality of adapters which can be combined to form a system for closing openings in tissue, wherein the adapters are configured to be detachably received on a medical instrument thereby altering the cross-sectional profile of a medical instrument utilized to close the opening. An exemplary embodiment of an adapter in accordance with the present invention includes a generally elongated member having a proximal and a distal end and a medical instrument holding portion, wherein the generally elongated member additionally includes at least one shim portion, the shim portion forming an enlarged cross-sectional area adjacent the medical instrument holding portion. The adapter may further include an aperture formed along the length of the elongated member, wherein the aperture is configured to receive a portion of the medical instrument therethrough. The present invention may further include a removable sheath which may be configured to be attached to a distal end or be received by the distal end of the medical instrument. Reference will now be made in detail to the present preferred embodiments of the invention, examples of which are illustrated in the accompanying drawings. The method and corresponding steps of the invention will be described in conjunction with the detailed description of the apparatus.

A variety of medical instruments are suitable for use with the apparatuses of the present invention. For purpose of illustration and not limitation, medical instrument 10 is depicted herein as a suturing instrument for suturing or closing openings in tissue. An example of a suitable suturing instrument can be seen in U.S. Pat. No. 6,136,010, wherein the suturing instrument includes a handle portion, a distal shaft and an articulating foot member, wherein the foot includes suture elements which are configured to be received by needles which descend from the handle portion, thereby forming a loop of suture across an opening in which the medical instrument 10 has been disposed therethrough.

Figure 5:
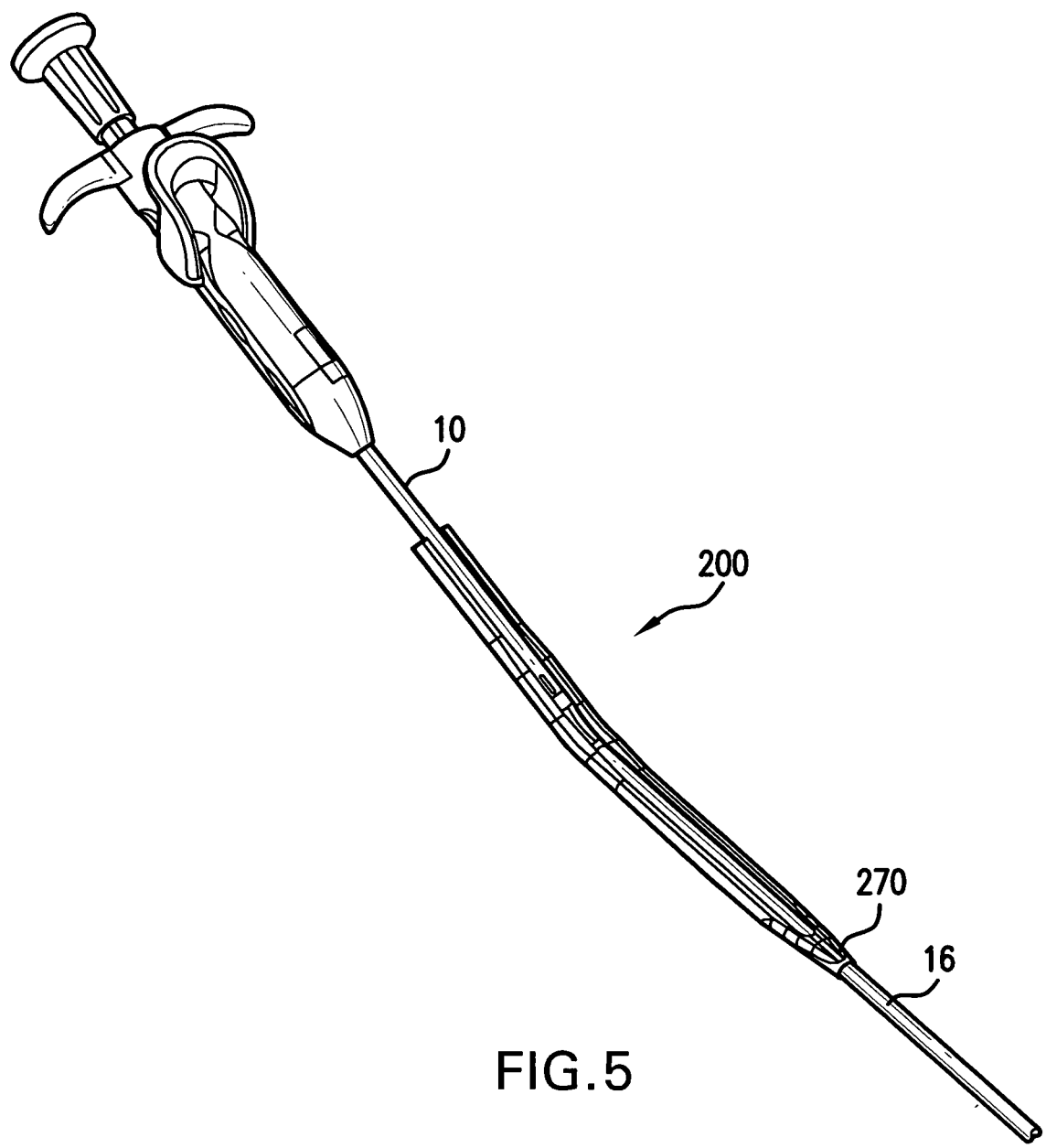
FIG. 5 is a top perspective view of an exemplary embodiment of the adapter of FIG. 3 in accordance with the present invention.

Referring now to FIG. 1, there is illustrated an exemplary embodiment of an adapter 100 in accordance with the present invention. As shown in FIG. 1, the adapter 100 comprises an elongated body member 110 having a proximal end 102, central portion 103 and a distal end 104, wherein the adapter 100 further includes a groove or instrument receiving portion 140, wherein as shown in FIG. 2, the adapter is configured to be received on the "left side" of an instrument (not shown) from an operator's perspective relative to the medical instrument. Referring now to FIG. 1, the adapter 100 further includes at least one shim portion 120 wherein the shim portion may be disposed along a portion of the elongated body or as shown in the embodiment of FIG. 5, along the entire length of the elongated body. Additionally, the shim portion 120 is disposed adjacent the medical instrument receiving portion 140. The shim portion 120 provides an enlarged peripheral surface 122 adjacent the medical instrument (not shown) such that when the medical instrument is held in the instrument holding portion 140 and the medical instrument 10 and adapter 100 are inserted through an opening in a patient tissue at least a portion of the enlarged peripheral surface 122 may be in contact with at least a portion of the periphery of the opening in the patient tissue.

A cutout, relieved portion, and/or aperture 124 may be provided at a location along the length of the elongated member 110, wherein the portion 124 may be configured to receive a guidewire or other instrument mechanism (not shown) to extend from the medical instrument as may be necessary. A bore 170 is optionally provided at the distal section 104 for accepting a distal sheath portion of a medical instrument upon mounting the adapter 100 on the medical instrument.

Referring now to FIG. 2, there is shown a cross-sectional view of the exemplary adapter taken about line 2-2 of FIG. 1. As shown in FIG. 2, the adapter 100 may further include a lumen 112 disposed within the shim portion 120 and extending at least partially therethrough and being configured to receive a guidewire or other medical device therein. The lumen 112 may also be configured to function as a blood marking lumen to allow a small amount of blood to flow through under pressure to an exit port disposed adjacent to the proximal end 102 (not shown), thereby providing visual feedback of placement of the adapter during use as will be described in greater detail below with regard to the methods of the present invention.

As shown in FIG. 2, the instrument holding portion 140 may additionally include an instrument engaging feature 150 or means for engaging the instrument (not shown) to hold the adapter 100 onto the medical instrument during use. An example of an instrument engaging feature is depicted in FIG. 2 as a protrusion 152 that can be shaped to engage a corresponding detent in the body of the device, for example. Other embodiments of an instrument engaging feature may include a detent or indentation or a frictional surface, for example. Alternatively, the adapter 100 may be constructed wherein the medical instrument receiving portion 140 is resilient, therefore, the instrument receiving portion 140 is configured to "snap around" and receive the medical instrument 10. Alternatively, the medical instrument 10, may additionally include features formed thereon wherein the features formed onto the medical instrument and features formed on the adapter would be configured to receive each other, thereby removably affixing the adapter to the medical instrument.

Figure 3B:
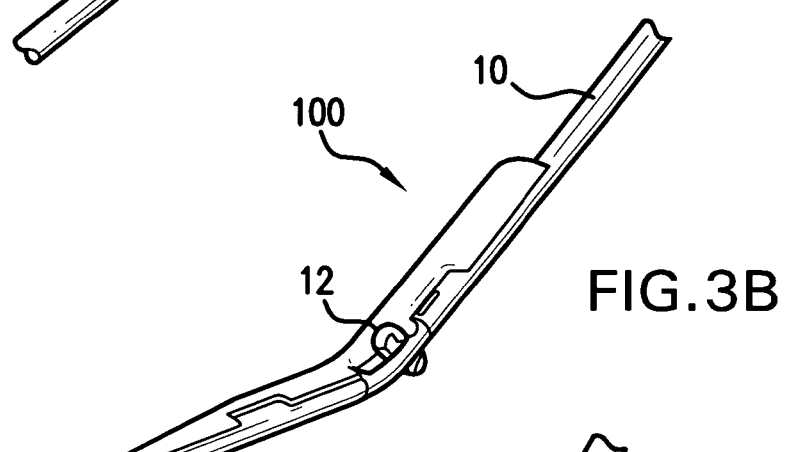
FIG. 3b is a perspective view of a medical instrument and an adapter in accordance with the present invention.
Figure 3A:
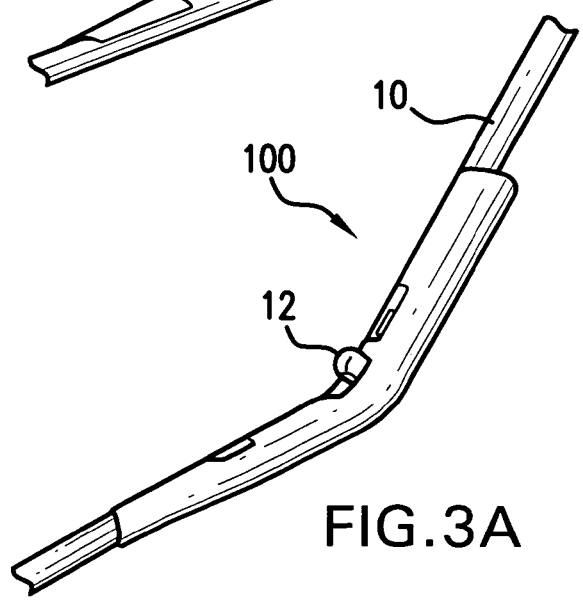
FIG. 3a is a perspective view of a medical instrument and an adapter in accordance with the present invention.

Referring now to FIGS. 3a, 3b, and 3c there are shown exemplary embodiments of various configurations of adapters 100 embodying the present invention. FIG. 3a shows an adapter 100 that is held or mounted on the "left side" of an instrument 10. FIG. 3b shows an adapter 100 that is held or mounted on the "right side" of an instrument 10. FIG. 3*c* shows an adapter 100 that is held or mounted on top of the instrument 10 such that the instrument is generally disposed over an upper surface, around the sides of, or surrounding a portion of the medical instrument when viewed from an operator's perspective. In each of the Figures, the retractable foot 12 of the medical instrument 10 is shown in a deployed position. It is contemplated that a special introducer sheath having an appropriate cross-sectional profile and a hemostatic valve may be used together with the adapters shown in FIGS. 3*a*, 3*b*, and 3*c* such that two or more sutures can be placed to close an opening in tissue as will be described and shown below with regard to the method of use of the present invention. The use of a special introducer sheath would allow the exchange of multiple medical instruments during a surgical procedure while preventing excessive blood loss during the removal and placement of each medical instrument and corresponding adapter.

Figure 4:
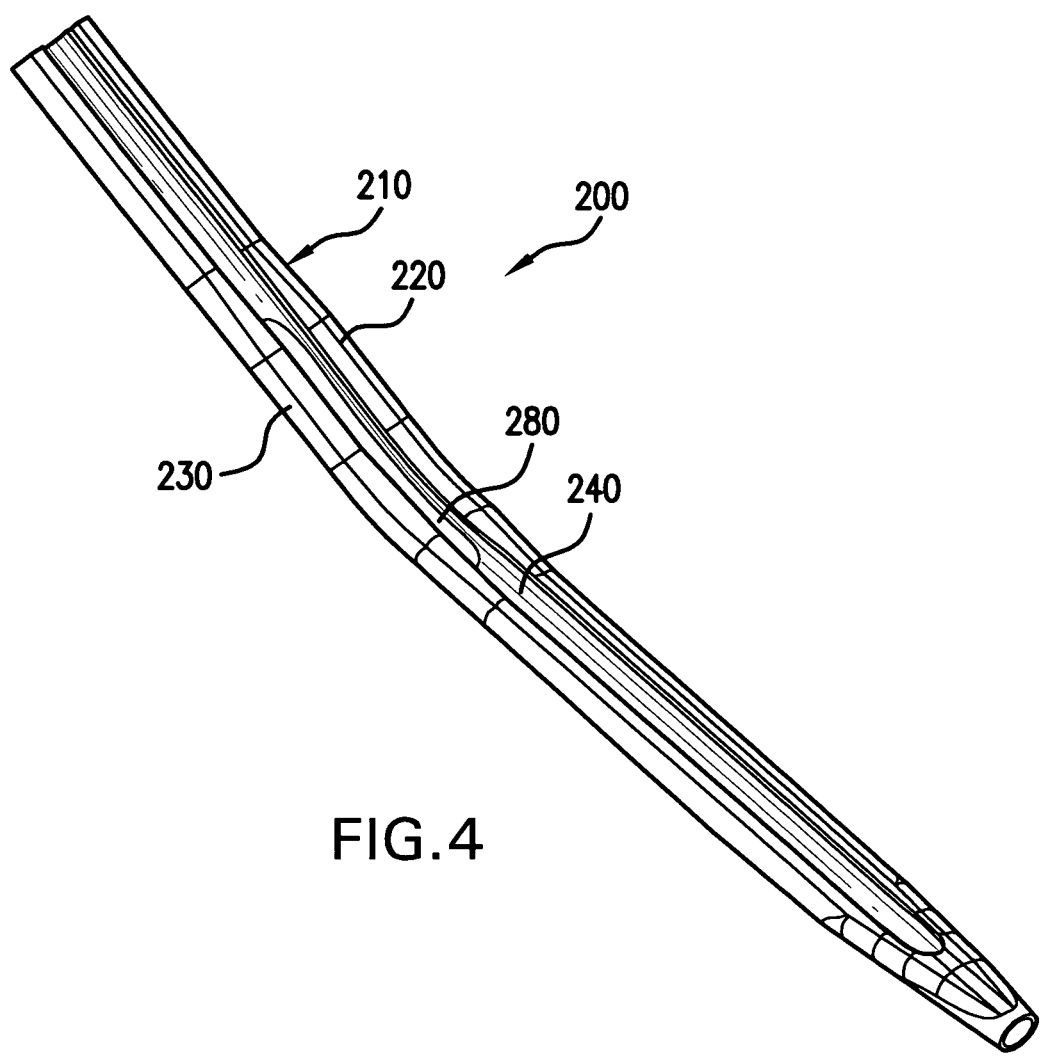
FIG. 4 is a perspective view of an exemplary embodiment of the adapter of FIG. 3 in accordance with the present invention.
Figure 6:
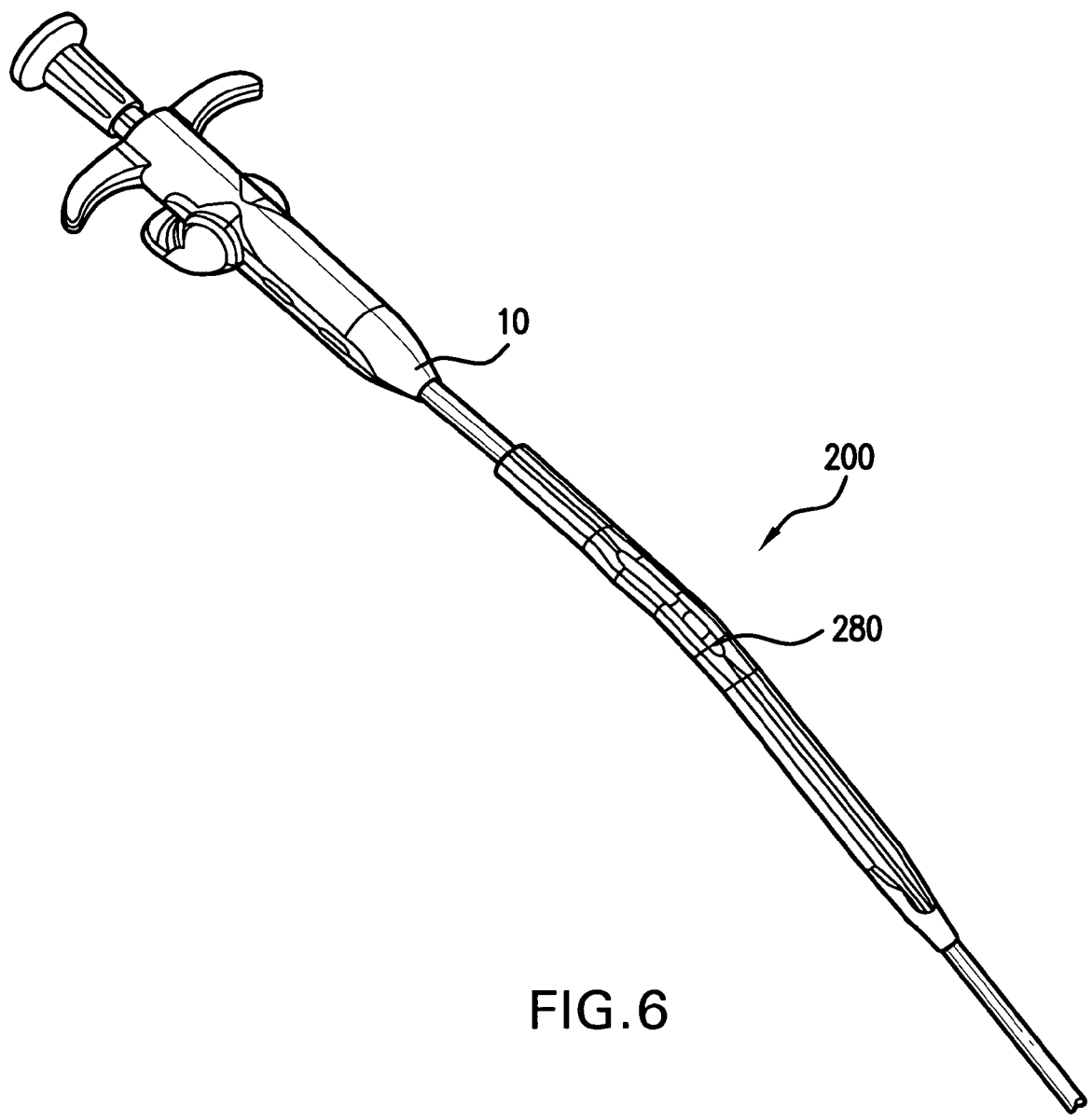
FIG. 6 is a bottom perspective view of an exemplary embodiment of the adapter of FIG. 3 in accordance with the present invention.

Referring now to FIGS. 4, 5, and 6 there is shown an alternative embodiment of an adapter in accordance with the present invention, as shown in FIG. 4, the adapter 200 is configured to hold an instrument in a "centered" orientation relative to the opening formed in the tissue. Adapter 200 includes a body 210 having a first shim portion 220 and a second shim portion 230. The instrument holding portion 240 extends centrally between the first and second body portions. An aperture 280 is defined through the body 210 in the instrument holding portion 240. It should be noted that the instrument holding portion 240 can be offset from the center of the body 210 as well as centered in the body. FIG. 5 illustrates the adapter 200 mounted or held on a medical instrument 10. The medical instrument 10 includes a distal section 16 extending through a bore 270 of the adapter 200. FIG. 6 shows an underside view of the adapter 200 and instrument 10 of FIG. 5. Aperture 280, shown in FIG. 6, provides an aperture through which a medical instrument mechanism such as a foot 12 can be extended.

Figure 7:
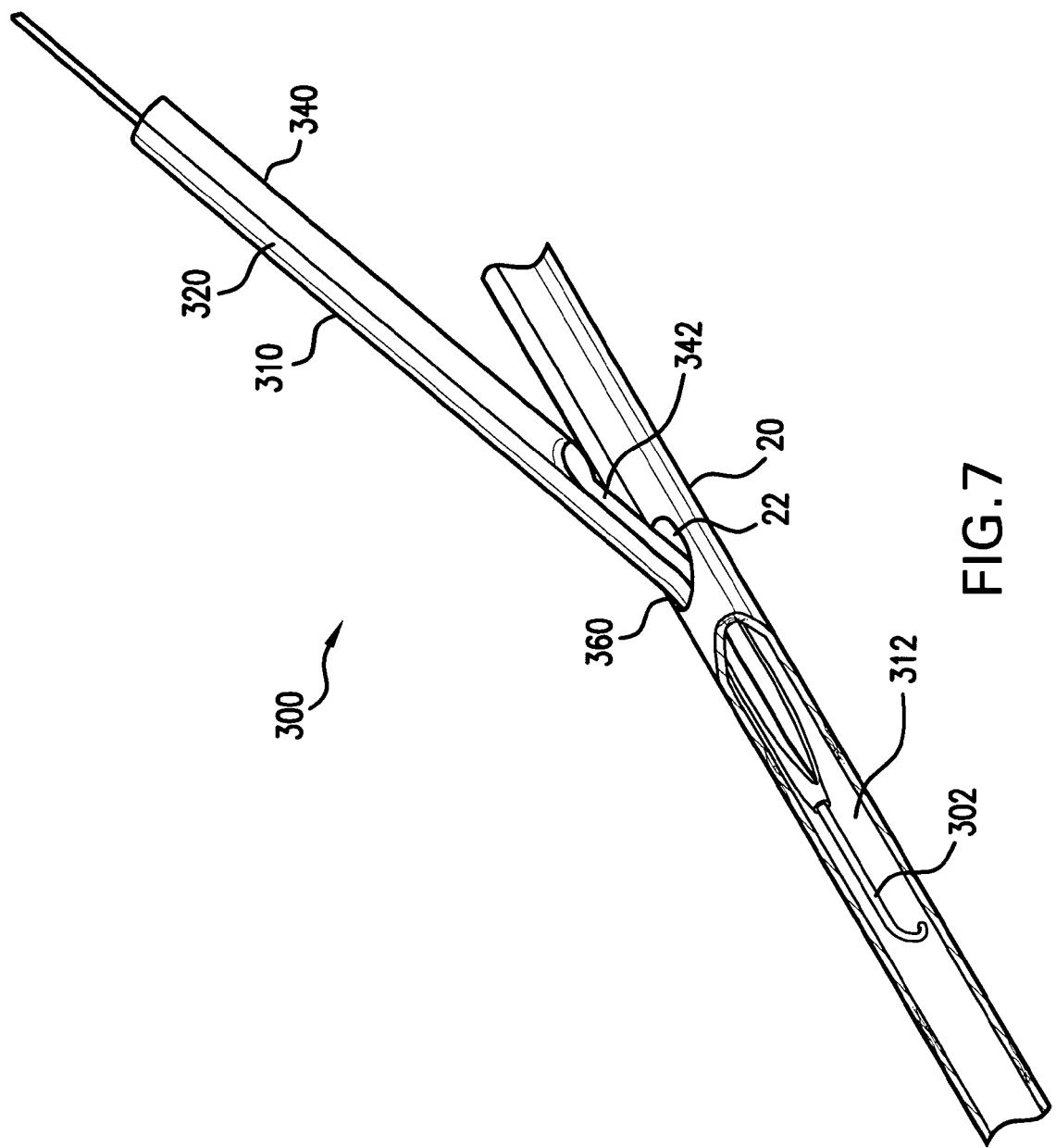
FIGS. 7, 8, 9, and 10 are perspective views of an alternative embodiment of an adapter in accordance with the present invention as inserted into an opening formed in tissue.

Referring now to FIGS. 7-10 there is illustrated yet another alternative embodiment of an adapter in accordance with the present invention. As shown in FIGS. 7-10, the adapter 300 as shown in FIG. 7 includes a body 310 having a shim portion 320 and an instrument holding portion 340. In this embodiment, instrument holding portion 340 defines an enclosed instrument lumen 342, rather than an open groove such as in the embodiments previously describe. The enclosed instrument lumen 342 may include a hemostatic valve.

Figure 8:
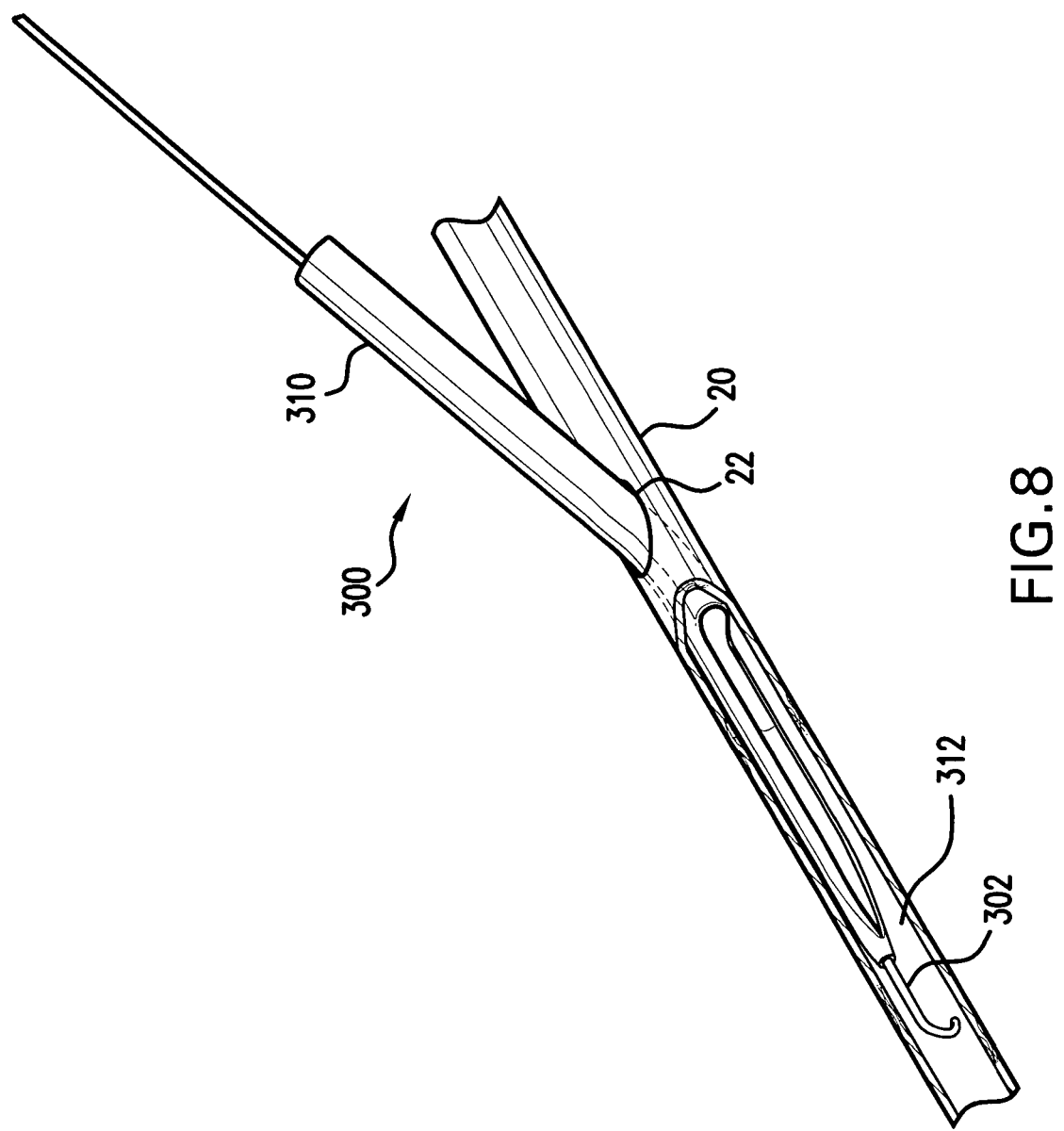

The body 310 further includes a distal extension 360 extending longitudinally from the shim portion 320. A guidewire lumen 312 may be defined through the distal extension 360 and shim portion 320. A guidewire 302 is shown extending through the guidewire lumen 312. The adapter 300 is first advanced along the guidewire and into the opening 22 of the vessel 20. FIG. 8 shows the adapter 300 in place.

Figure 9:
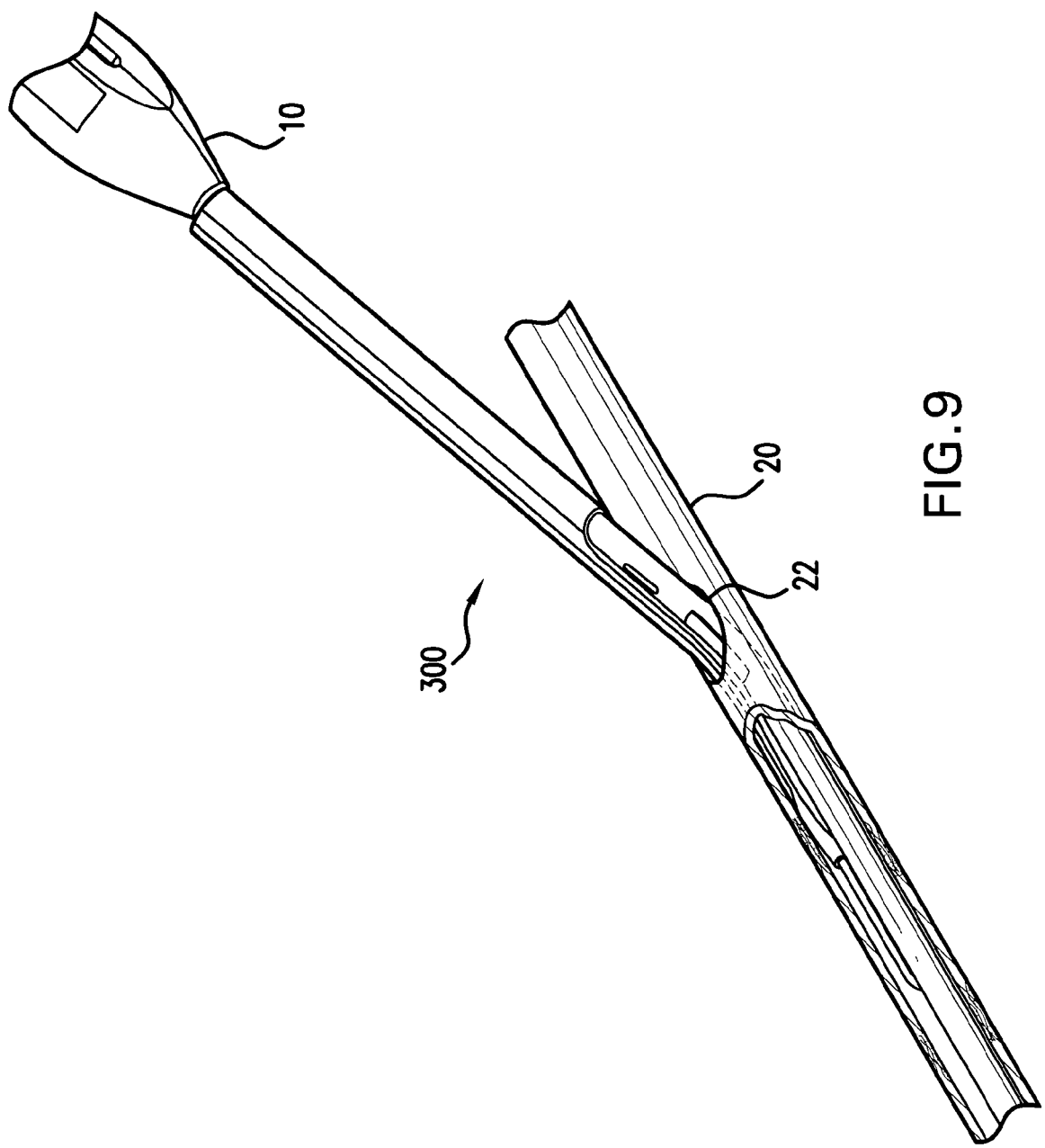

FIG. 9 shows an instrument 10 inserted into the adapter 300 and further into the vessel 20. At this stage, the instrument 10 can be deployed to place a suture across the opening 22. The instrument is then removed from the adapter 300, leaving the adapter in place in the opening.

Figure 10:
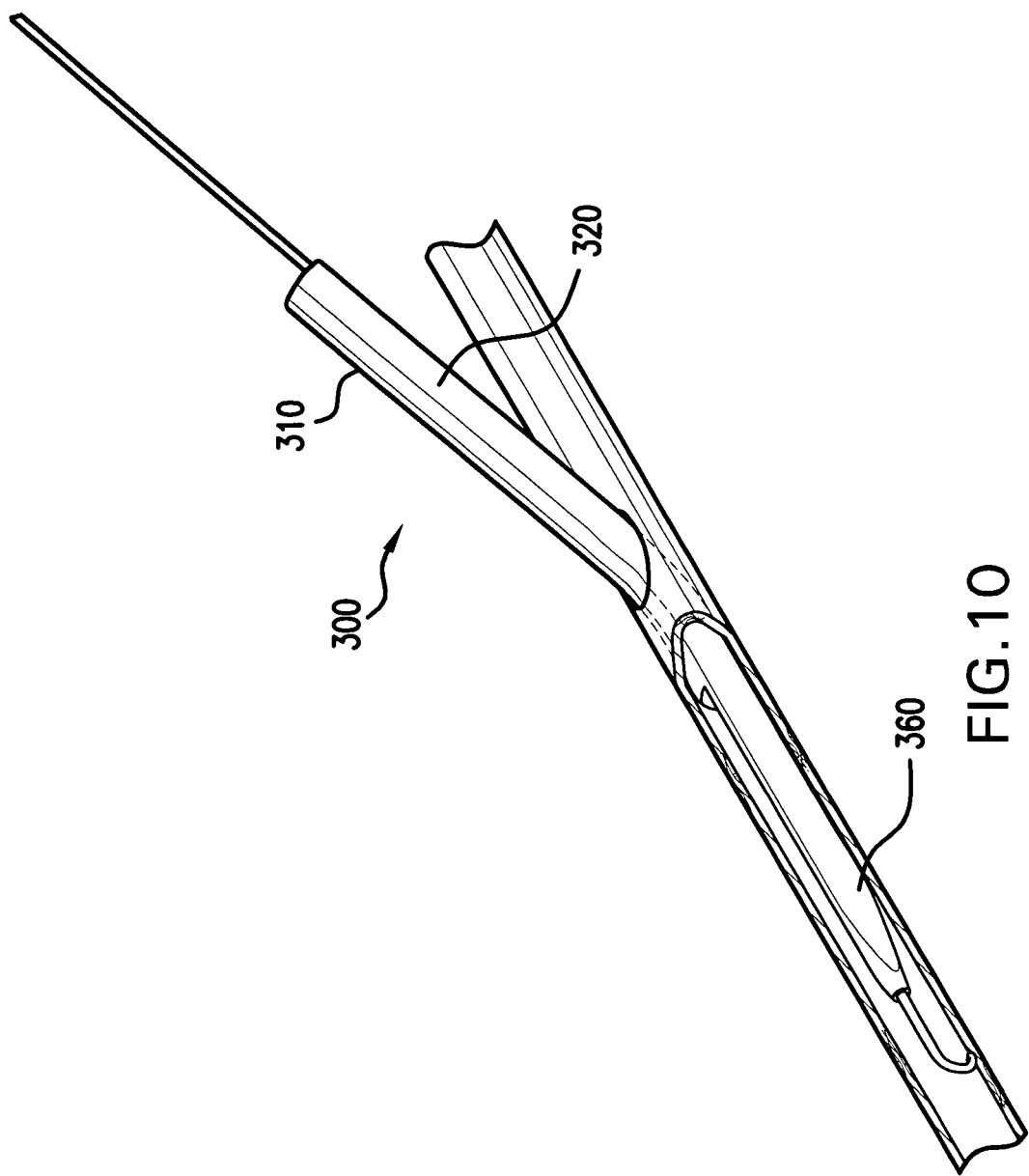

FIG. 10 shows the adapter 300 after it has been rotated 180 degrees to position the shim portion 320 and distal extension on the opposite side of the vessel. A second instrument (not shown) can be then advanced through the adapter to place a second stitch parallel to the first stitch.

Figure 11:
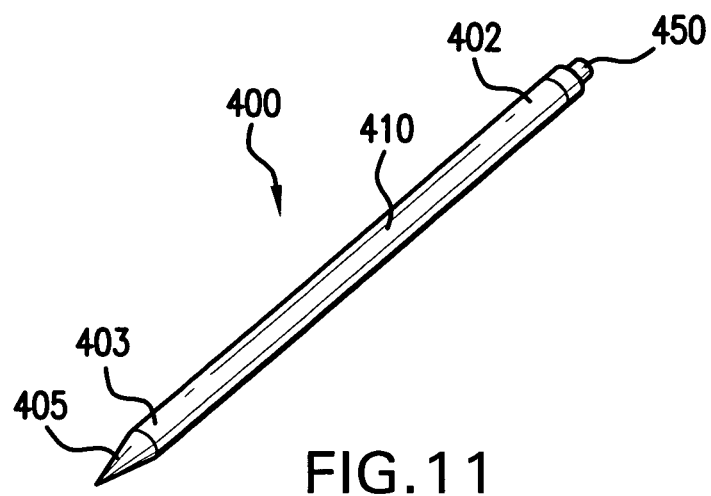
FIG. 11 is perspective view of an alternative embodiment of a connection element and distal sheath in accordance with the present invention.
Figure 12:
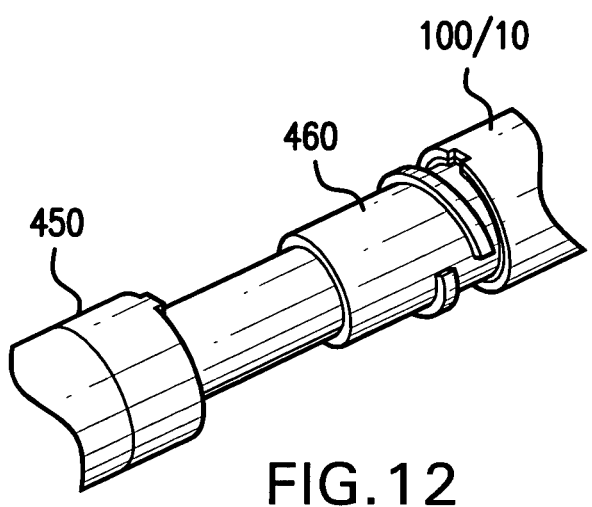
FIG. 12 is a perspective view of the adapter, distal sheath and a medical instrument of FIG. 11.
Figure 13:
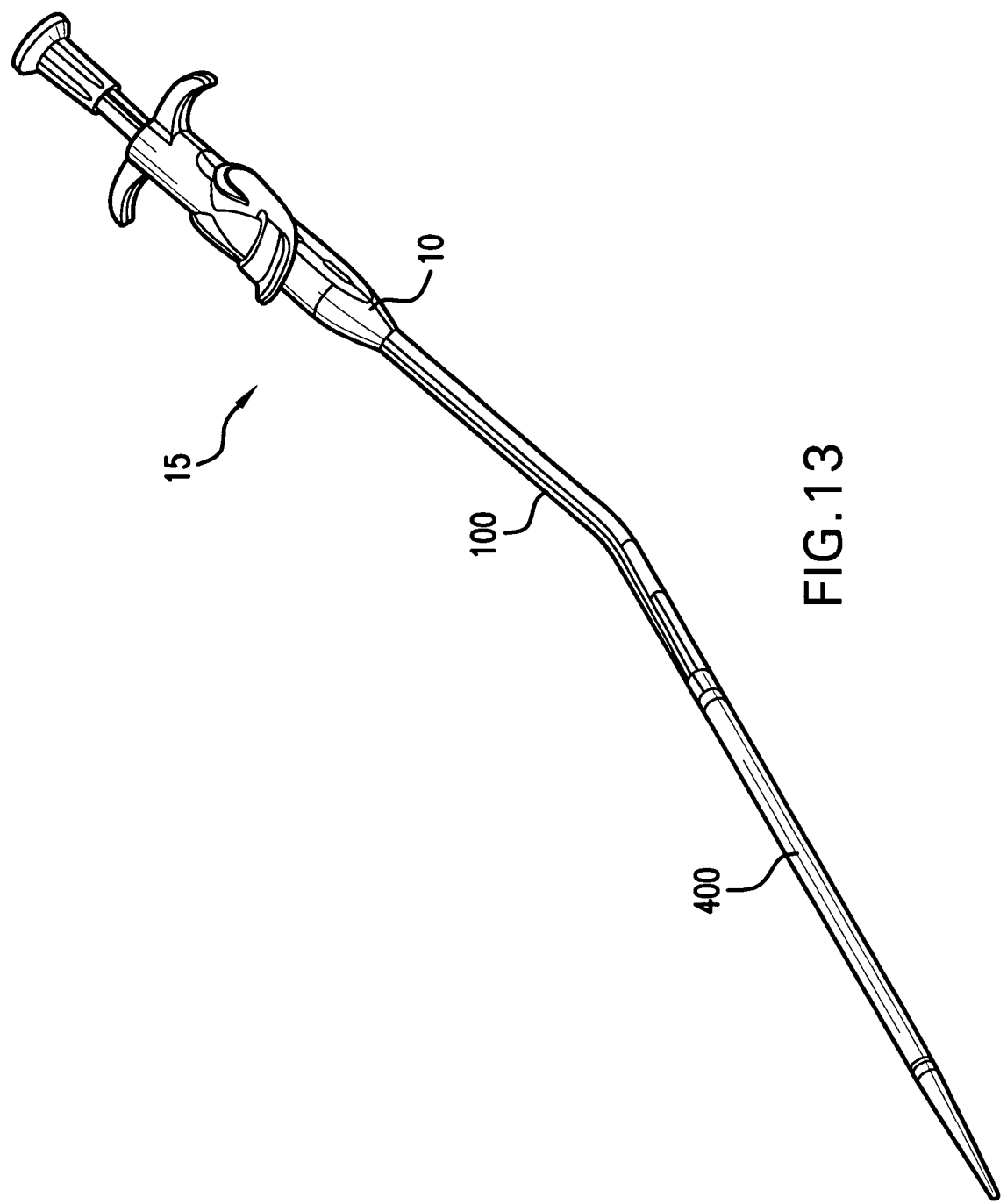
FIG. 13 is a perspective view of the adapter of FIG. 11 and a medical device in accordance with the present invention.

Referring now to FIGS. 11-13, there is shown a removable sheath assembly which may be utilized in combination with the adapters shown and described above in FIGS. 1-10. The removable sheath includes an elongated body having a proximal end, a distal end, and a tapered portion adjacent the distal end, wherein a bore extends from the proximal end to the distal end, a guidewire lumen may extend through the tapered distal tip, wherein a hemostasis valve may be additionally disposed in the tapered distal tip or anywhere along the bore of the removable sheath. It is further contemplated that an additional guidewire/marker lumen may extend between the distal tip/end and the proximal end. The removable sheath further includes a connection element disposed adjacent to the proximal end thereof, the connection element configured to detachably attach the proximal end of the removable sheath to a medical instrument, wherein the medical instrument includes a similar connection element.

Referring now to FIG. 11 there is shown an exemplary embodiment of the distal sheath 400 in accordance with the present invention. As shown in FIG. 11, the distal sheath 400 comprises and elongated member 410 having a proximal end 402, a distal end 403 and a tapered distal tip 405, a bore 406 (not shown) extends from the proximal end to the distal end, wherein the bore is configured to receive a distal end of a medical instrument as will be shown and described in greater detail with regard to the methods of the present invention. The tapered distal tip may further include a lumen therethrough (not shown) wherein the lumen may be configured to receive a guidewire or function as a marker lumen. The distal sheath 400 may further include a hemostasis valve, wherein the hemostasis valve may be disposed at any location along the length of the elongated member and including the tapered distal tip. A second lumen may be disposed along the length of the elongated member 410, wherein the second lumen would be generally parallel to the bore and may be utilized as a marker lumen or a guidewire lumen.

As described above, the distal sheath 400 further includes a connection element 450, wherein the connection element 450 is disposed adjacent the proximal end 402 of the distal sheath. The connection element is configured to engage a similar connection element disposed on the medical instrument 10 or adapter 100, thereby detachably attaching the distal sheath 400 to the medical instrument 10 or adapter 100.

Referring now to FIG. 12, there is shown an exemplary embodiment of a connection element 450 in accordance with the present invention. As shown in FIG. 12, the connection element 450 disposed on the distal sheath 400 comprises a female threaded member, wherein the connection element 460 disposed on the adapter 100 and/or medical instrument 10 comprises male threads, wherein the female threaded portion of the connection element 450 is configured to engage the male threaded portion 460 of the adapter/medical instrument thereby allowing the two pieces to be detachably attached, thereby forming a medical instrument 15 as shown in FIG. 13, wherein the medical instrument 15, comprises distal sheath 400, adapter 100 and a medical instrument 10, wherein the adapter 100 may comprise a "left, center, or right" adapter as described in detail above.

As shown in FIGS. 11-13 and described in detail above, the second connection element 460 may be disposed on the medical device 10 or alternatively upon the adapter 100. By placing the second connection element upon the adapter 100, the adapter and distal sheath may be utilized with any medical instrument which is compatible with the present invention. Additionally, this may lead to reduced costs as well being that a currently existing medical instrument may be utilized with the adapter and distal sheath rather than having to custom manufacture a different medical instrument.

Figure 14:
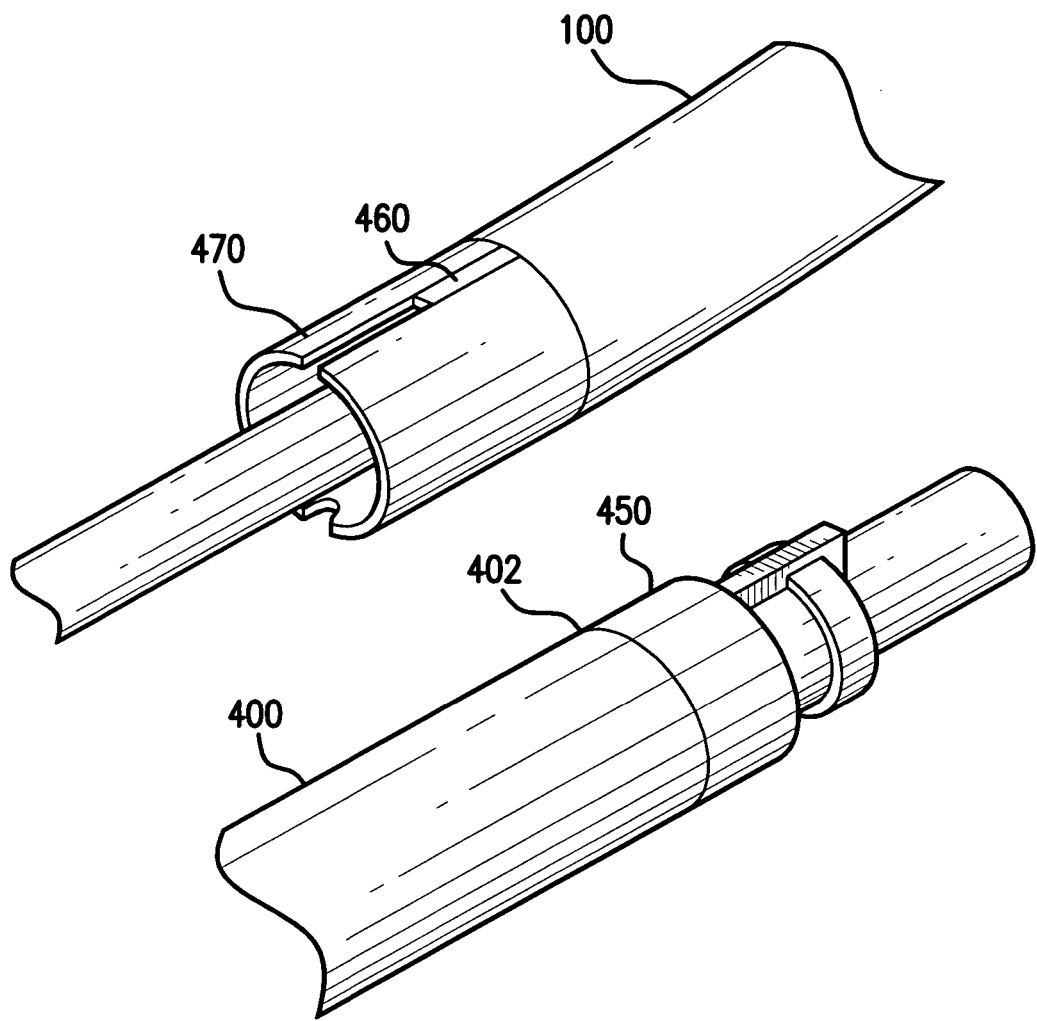
FIG. 14 is a perspective view of an exemplary embodiment of a connection element in accordance with the present invention.
Figure 15:
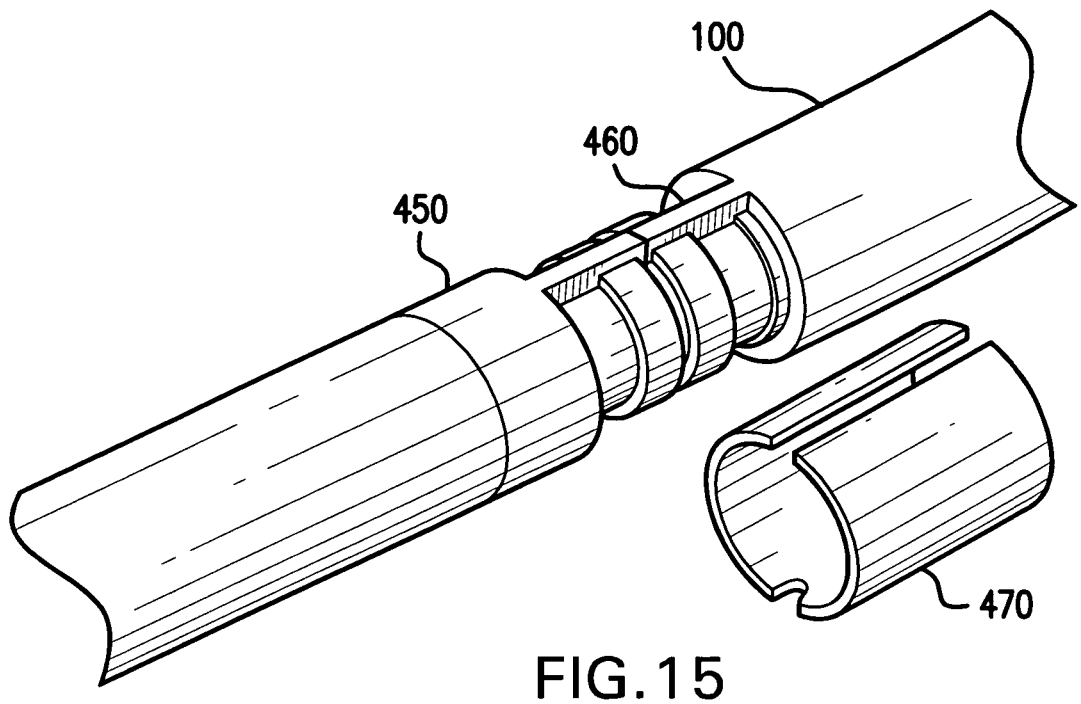
FIG. 15 is a perspective view of the connection elements of FIG. 14 and an exemplary embodiment of a clip according the present invention.

Referring now to FIGS. 14-17, there is shown an exemplary embodiment of preferred connection elements in accordance with the present invention. As shown in FIG. 14, a connection element 450 is shown disposed on the proximal end 402 of the distal sheath 400 and a second connection element 460 is shown disposed on the distal end of an adapter in accordance with the present invention, additionally a clip 470 is shown disposed on the connection element 460 associated with the adapter. As shown in FIG. 14, the adapter 100 has been detachably attached to a medical instrument 10, wherein the distal end of the medical instrument 10 extends through the connection element 460 and the clip 470, wherein the distal end of the medical instrument is configured to be received within the bore of the distal sheath 400 as shown in FIG. 15 (clip 470 omitted for clarity). As shown in FIG. 15, the first connection element 450 and the second connection element 460 are configured such that alignment elements disposed on the connection elements align the distal sheath and the adapter in proper alignment and provide means to transmit torque along the assembly.

Figure 16:
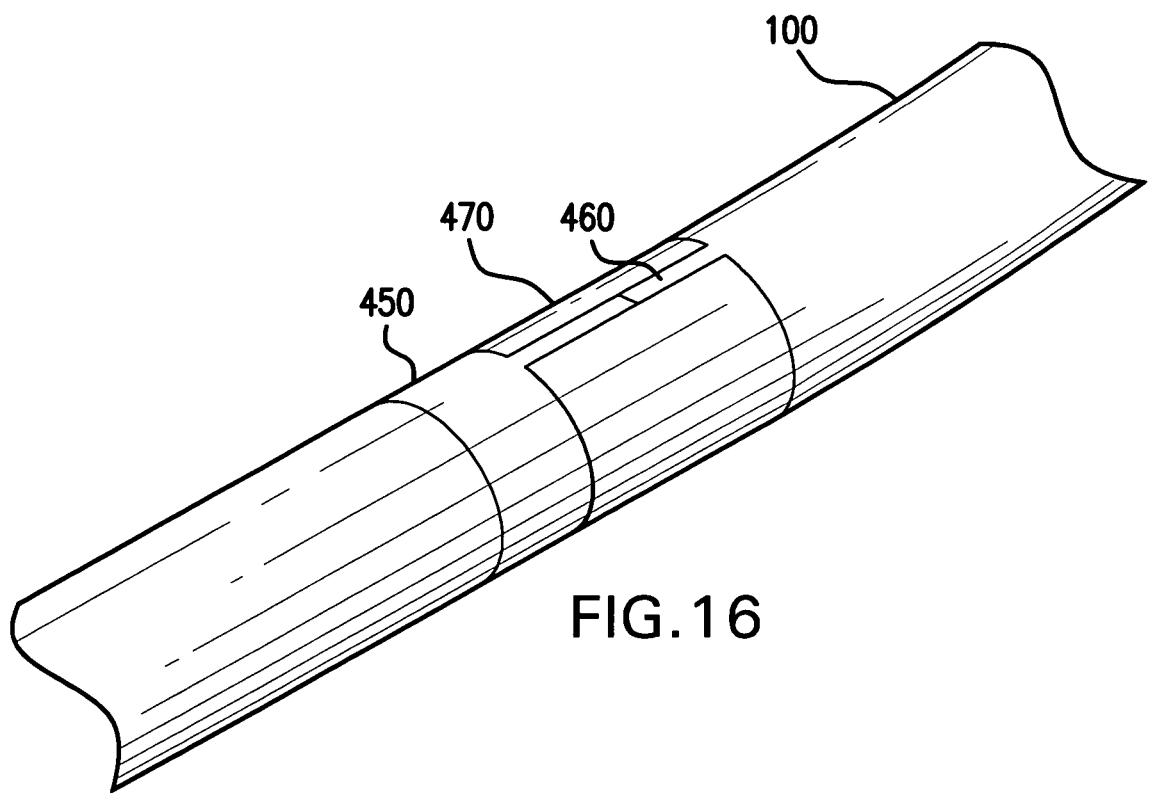
FIG. 16 is a perspective view of the connection element of the adapter and distal sheath wherein a clip is shown disposed thereabout to detachably attach the two connection elements.

As shown in FIG. 16, the clip 470 is configured to receive the first connector element 450 and the second connector element 460, wherein the clip detachably retains the two connector elements in an aligned position. The clip 470 is configured to retain the two connector elements with sufficient force such that the two connector elements cannot be easily separated during use. One of the two connector elements or both connector elements may be separated by applying a force to either the adapter or the distal sheath. As shown in FIGS. 14 and 16 the clip 470 is configured to have a low profile, equal to or substantially equal to that of the connector elements, adapter and/or distal sheath, such that in use the clip 470 does not present any sharp surfaces or enlarged surfaces which may cause procedural complications.

As shown in FIG. 16, the clip 470 is configured to received the first connector element 450 and the second connector element 460, wherein the clip detachably retains the two connector elements in an aligned position. The clip 470 is configured to retain the two connector elements with sufficient force such that the two connector elements cannot be easily separated during use. One of the two connector elements or both connector elements may be separated by applying a force to either the adapter or the distal sheath. As shown in FIGS. 14 and 16 the clip 470 is configured to have a low profile, equal to or substantially equal to that of the connector elements, adapter and/or distal sheath, such that in use the clip 470 does not present any sharp surfaces or enlarged surfaces which may cause procedural complications.

Figure 17:
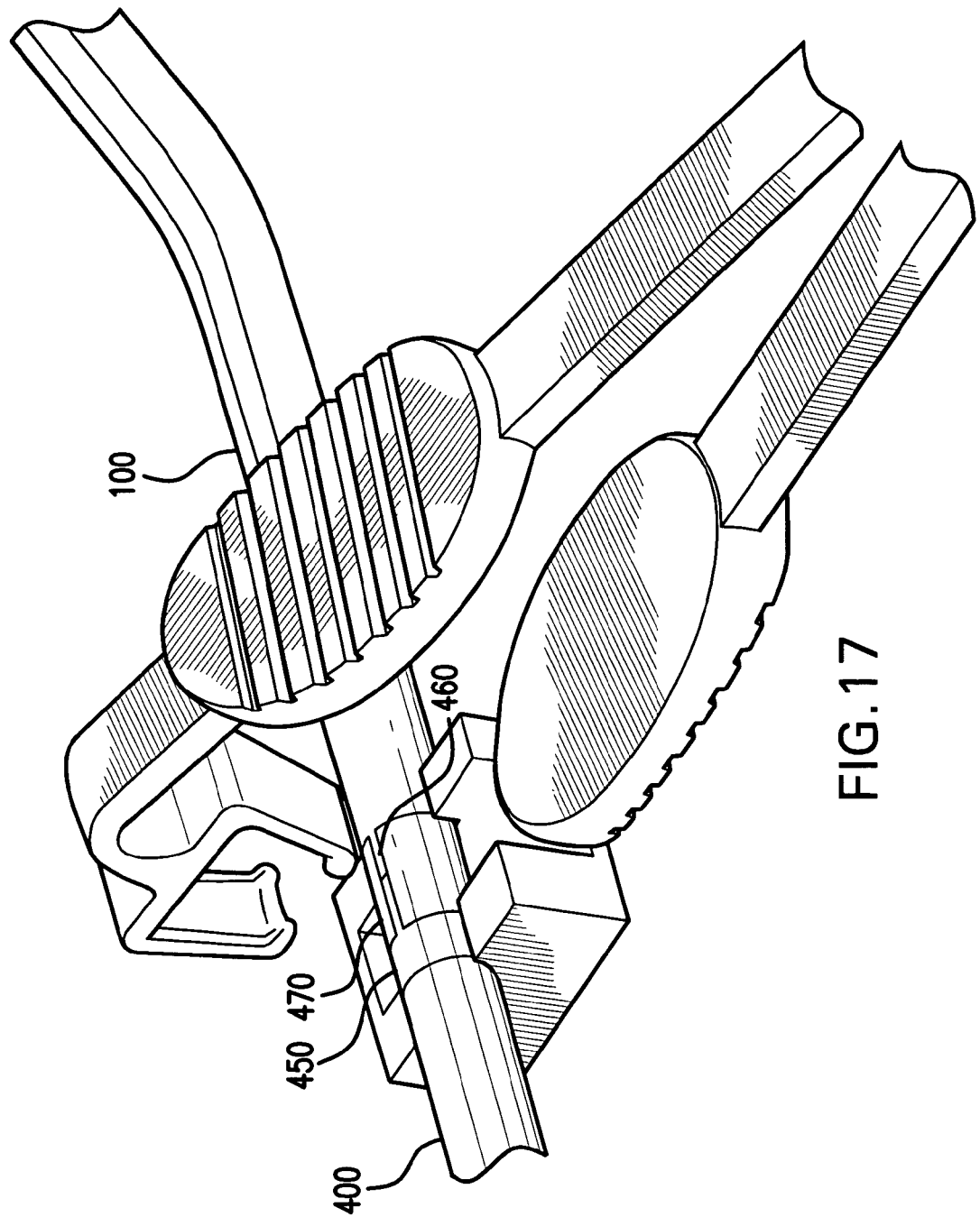
FIG. 17 shows an exemplary embodiment of a clip tool according to the present invention.

In a preferred embodiment, a clip tool 500 is utilized to detach the first and second connector elements, wherein the clip tool 500 may also be utilized to remove a clip which retains the first and second connector elements. An exemplary embodiment of a clip tool is shown in FIG. 17, wherein the clip tool includes a first member including a first clip engaging portion and a second member including a clip engaging portion, wherein the first and second members oppose one another and may include a biasing member to retain the first and second members in a biased position. In use, the clip is placed in the first clip engaging portion and the second clip engaging portion is advanced, wherein the second clip engaging portion engages the clip, thereby opening the clip such that the first and second connection elements may be disengaged from each other. It shall be understood that the embodiments of the clip, connector elements and clip tool should be considered exemplary, in that each of these elements may be constructed in a different manner yet retain similar functionality, and the embodiments shown in the appended drawings and described herein should not be considered limiting in any manner.

It is further contemplated that other connection elements may be utilized to perform the same or similar function of the clip and connection elements described above. For example, it is contemplated that a connector element may be configured wherein the connection element comprises a male and female element wherein one of the elements can be detached from the other through the use of an applied force. The applied force may be applied longitudinally, axially, or along any axis of the adapter, distal sheath, medical instrument, and the like.

In accordance with the present invention, methods of use of the present invention will be described in greater detail, with reference to additional figures and embodiments of the present invention.

Referring now to FIGS. 18-21, there is shown the apparatuses of the present invention in use, wherein exemplary embodiments of each of the elements of the present invention are shown in use to close an opening formed in tissue.

Figure 18:
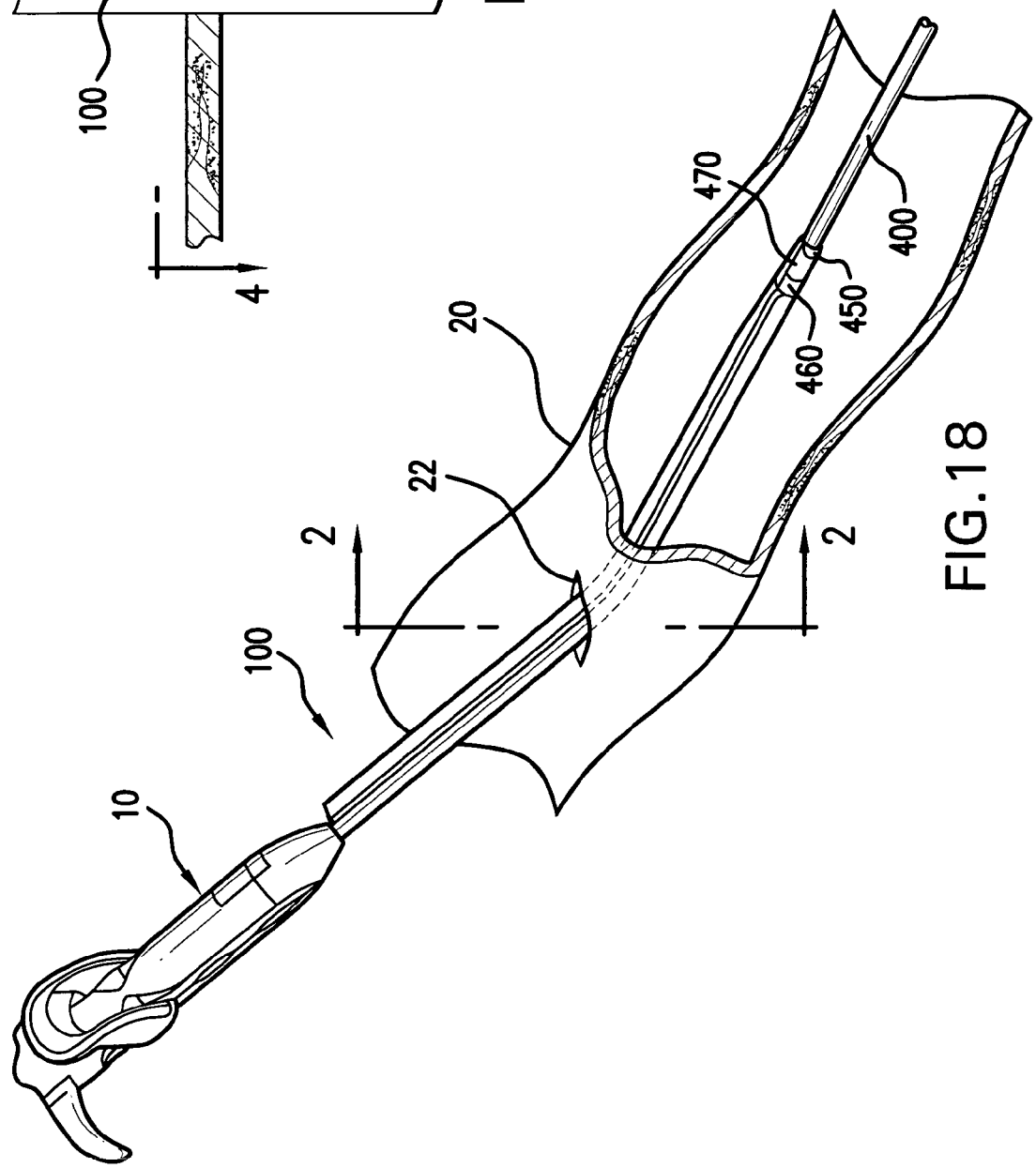
FIG. 18 shows a left-side adapter and distal sheath mounted to a medical instrument, wherein the adapter, distal sheath and medical instrument are shown disposed in a tissue opening.

As shown in FIG. 18, a "left" adapter 100 is shown to be mounted to a medical instrument 10, and distal sheath 400 is shown attached to the distal end of the adapter 100. As shown in FIG. 18 the medical instrument 10 together with the adapter 100 have been positioned through an opening 22 in a vessel wall 20.

Figure 19:
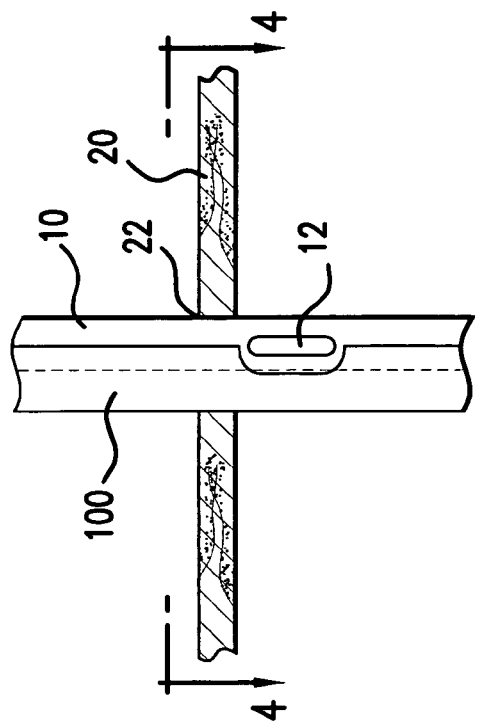
FIG. 19 shows a right side offset adapter mounted to a medical instrument as disposed through a tissue opening.

Referring now to FIG. 19, there is shown an enlarged view of the portion of the medical instrument and adapter according to the present invention as indicated by line 2-2 of FIG. 18. As show in FIGS. 18 and 19, the adapter 100 is shown mounted to the left side of the instrument 10, in this exemplary embodiment. The instrument mechanism 12 can be an articulating "foot," or needle ports as described in detail above with reference to the medical instrument 10.

Figure 20:
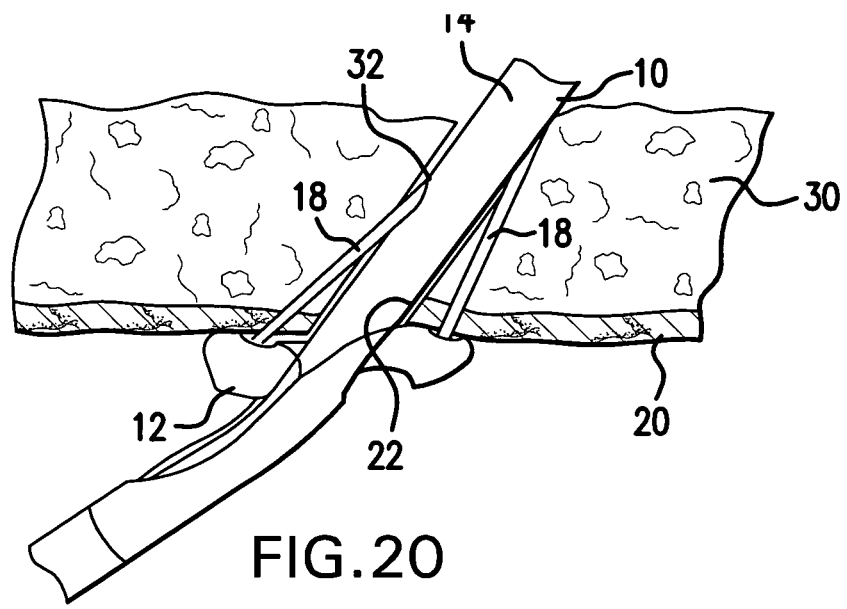
FIG. 20 is a partial view of a medical instrument which may be utilized with the present invention.

FIG. 20 shows the instrument 10 positioned through subcutaneous tissue 30 of a patient. The subcutaneous tissue 30 has a tissue tract 32 formed therein, which is a hole at the bottom of which is the opening 22 of the vessel wall 20. Instrument 10 is shown with its foot or instrument mechanism 12 deployed and needles 18 extending from the proximal shaft 14 of the instrument 10 to the mechanism 12. The structure and operation of the instrument 10 is described more fully in U.S. Pat. No. 6,136,010, the full disclosure of which is incorporated herein by reference.

Figure 21:
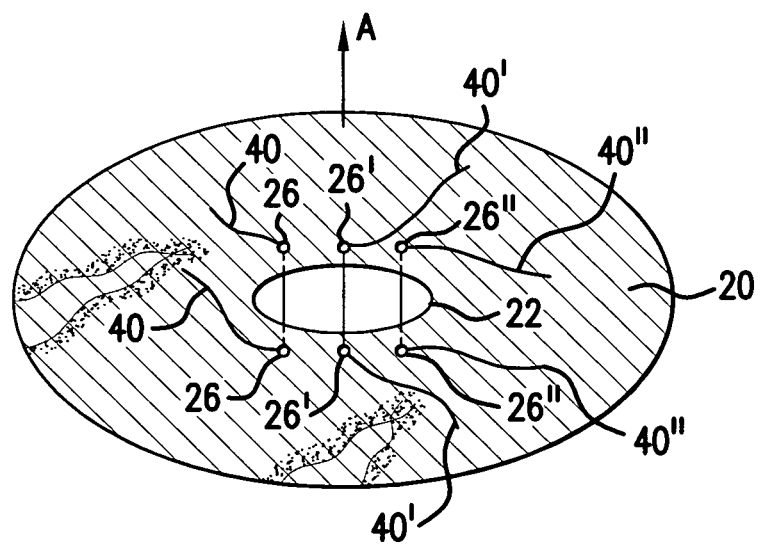
FIG. 21 is a top view of the tissue opening illustrating the multiple suture elements that may be placed to close the opening using the methods and devices of the present invention.

FIG. 21 shows examples of suture patterns across an opening 22 in a vessel wall 20. Pairs of needle punctures 26, 26', and 26" are shown in the vessel wall 20. Suture loops 40, 40', and 40" are shown extending through respective pairs of needle punctures. Each suture loop can be tied individually to provide a plurality of stitches across opening 22 to close the opening. The ends of the suture loops can be tied to non-corresponding ends to result in crossed stitch patterns or a pattern similar to a mattress stitch, as desired. It is further contemplated that the device and methods in accordance with the present invention may be utilized to partially close a large opening by placing at least one suture, after partially closing the opening, an additional medical procedure could be performed through the smaller opening, then the smaller opening can be closed using the methods and devices disclosed herein after completion of the procedure.

In use, the detachable distal sheath is inserted into the femoral artery over a guidewire in a manner similar to that of a common introducer sheath. When it is desired to use more than one instrument in order to place a plurality of sutures, the instruments are provided with adapters one at a time. After the first instrument is deployed, its adapter is detached from the distal sheath and the first instrument with attached adapter is removed from the distal sheath. The sheath remains in place to maintain hemostasis while an instrument exchange occurs. The above described method continues to occur until a sufficient number of sutures have been placed to close the opening in the tissue. For example, as shown in FIG. 21, a medical instrument having a first adapter would be inserted into the opening using a known technique, wherein a first suture would be deployed, the medical instrument would be withdrawn a sufficient amount from the opening to expose the clip. The clip would be removed from the device as described above, a second medical instrument may then be attached to the distal sheath using the clip, wherein the medical instrument would include an adapter having a profile differing from that of the previous adapter. The above process continues until a sufficient number of sutures have been placed to close the opening. After the final suture is placed, the medical instrument including the adapter and distal sheath may be removed from the opening while a tension force is applied to the sutures to control bleeding if required. If not, the medical instrument and adapter may be removed from the distal sheath, wherein the distal sheath may be utilized to maintain hemostasis.

It should be noted that the various embodiments of adapters can be used with other types of medical instruments, for example, stapling or other non-suture based vessel closure devices are contemplated for use with the adapter embodiments of the present invention. It is contemplated that the adapter(s), connector elements, clip, and distal sheath may be constructed of any material, in a preferred embodiment a biocompatible material is utilized. Additionally, any or all of the components of the present invention may include a coating, the coating may be embodied as a hydrophilic coating, a beneficial agent or any other biocompatible coating.

Figure 22:
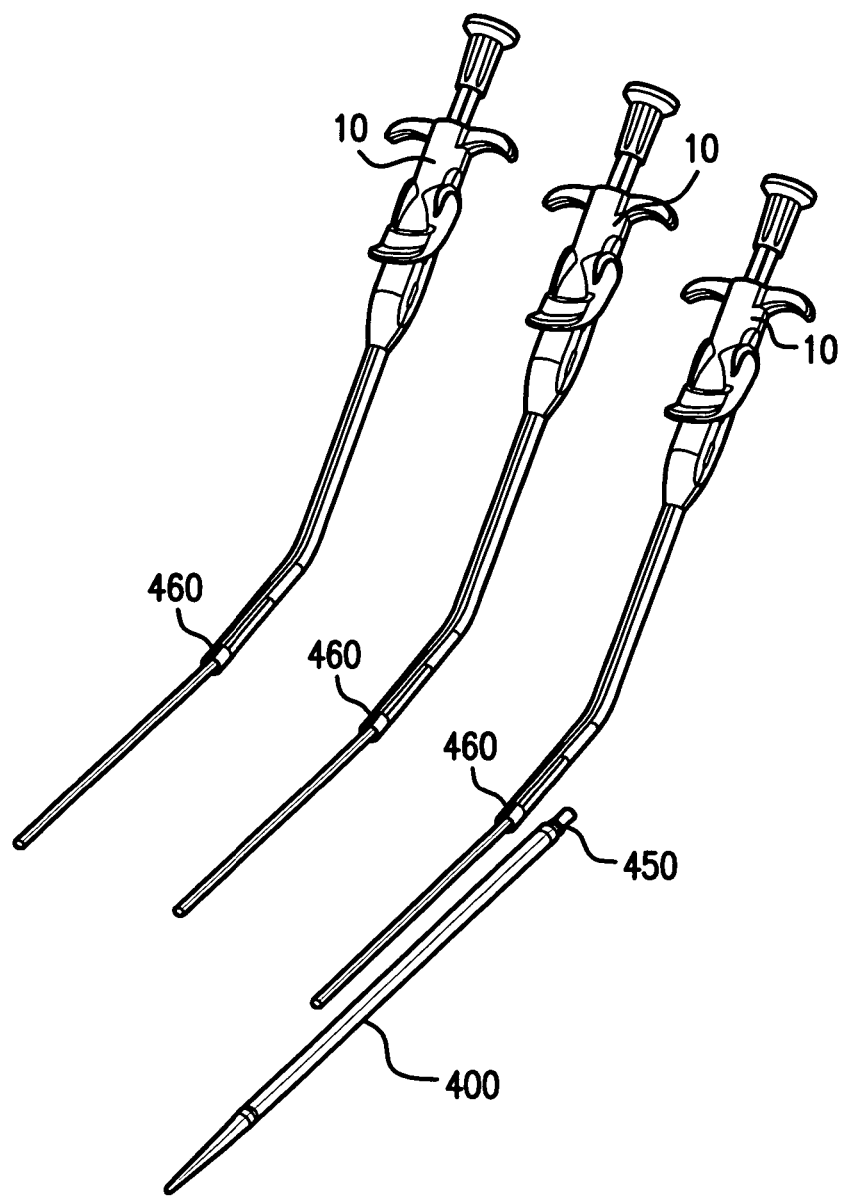
FIG. 22 is an isometric view of a kit in accordance with the present invention.

Referring now to FIG. 22 there is shown an exemplary embodiment of a kit in accordance with the present invention. The kit includes at least one medical instrument, and a distal sheath, wherein the medical instrument includes an integrated adapter in accordance with the present invention. In a preferred embodiment, the kit preferably includes at least two medical instruments and a distal sheath. The medical instrument of the kit illustrated in FIG. 22 is similar to the medical instrument described above and in U.S. Pat. No. 6,136,010 the entirety of which is herein incorporated by reference, and U.S. Patent Publication No. 2003/00093093 and U.S. patent Ser. No. 10/652,182, filed Aug. 29, 2003 and U.S. patent Ser. No. 10/660,288, filed Sep. 11, 2003 respectively, the entireties of which are herein incorporated by reference. The suturing instrument includes a handle portion, a distal shaft and an articulating foot member, wherein the foot includes suture elements which are configured to be received by needles which descend from the handle portion, thereby forming a loop of suture across an opening in which the medical instrument 10 has been disposed therethrough. As described above, each medical instrument of the kit includes an adapter integrally formed onto a distal section of the medical instrument, wherein each medical instrument includes an adapter having different geometry. For example, in exemplary kit illustrated in FIG. 22, wherein three medical devices are provided in the kit, each medical device would have an adapter having different geometry, for example, the medical instruments would have a left, right and center geometry as described in detail above. Additionally, as shown, the medical instruments would include a connector element 460 similar to that described above, wherein the sheath 400 would also include a connector element 450, the two connector elements configured to engage each other, wherein a separate clip may be utilized to retain the two connector elements, or alternatively, the connector elements may have geometry which is configured to retain the two connectors independent of a separate element.

In use, one of the medical instruments is chosen, the distal sheath is attached to the distal end of the medical instrument, wherein the assembly would then be inserted into an opening formed in a patients tissue, this may be accomplished by passing the assembly over a guidewire or through a sheath. After the medical instrument has been deployed and a suture has been placed adjacent the opening, the assembly is partially retracted from the opening until the connector elements are accessible. A tool, such as that shown in FIG. 17 may be used to separate the distal sheath from the medical instrument. The medical instrument may then be retracted from the distal sheath, wherein the distal sheath remains within the opening to provide hemostasis. A second medical instrument having a different adapter profile may then be attached to the distal sheath and the assembly advanced into the opening, wherein a second suture is deployed adjacent to the opening. This process may be repeated a number of times until a sufficient number of sutures have been placed adjacent the opening to provide sufficient closure of the opening. Once a sufficient number of sutures have been placed, the final assembly (medical instrument and distal sheath) is then removed from the opening, knots may be formed and the opening may be closed.

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed is:

1. An adapter for a suturing device, the adapter comprising: a body having a proximal end, a distal end, a shim portion, and an instrument holding portion adjacent the shim portion, the instrument holding portion having an inner surface and an opposing peripheral outer edge, the inner surface bounding a groove extending longitudinally along the body, at least a first engagement feature being formed on the inner surface of the groove that is complementary to at least a second engagement feature formed on the suturing device, the first and second engagement features being configured to receive one another, the engagement of the first and second engagement features removably affixing the adapter to the suturing device, the shim portion being configured to provide an enlarged peripheral surface adjacent the suturing device, the suturing device being held in the groove so as to protrude laterally out of the groove and laterally beyond a first portion of the peripheral outer edge of the instrument holding portion when the suturing device and body are inserted through an opening in a patient tissue, the first portion being located proximally of the distal end and distally of the proximal end, the first portion being laterally aligned with the first engagement feature, the enlarged peripheral surface and the surface of the suturing device at the first portion of the peripheral outer edge of the instrument holding portion being capable of contacting at least a portion of the periphery of the opening in the patient tissue.

2. The adapter of claim 1, wherein the shim portion of the adapter has a longitudinal axis generally aligned parallel to a longitudinal axis of the suturing device.

3. The adapter of claim 1, wherein the shim portion of the adapter has a longitudinal axis generally aligned vertically to a longitudinal axis of the suturing device.

4. The adapter of claim 1, wherein the adapter comprises a generally elongate member having a first shim portion adjacent a proximal end, a second shim portion adjacent a distal end and a reduced cross-sectional area disposed between said two shim portions.

5. The adapter of claim 1, wherein the adapter is constructed of a flexible material wherein the adapter is configured to mimic a profile of the suturing device.

6. The adapter of claim 1, the adapter further including a second adapter, the second adapter having a second body having a second shim portion and a second instrument holding portion adjacent the second shim portion, wherein the second shim portion provides a second enlarged peripheral surface adjacent the suturing device such that when the suturing device is held in the second instrument holding portion and the suturing device and the second body are inserted through the opening in the patient tissue, at least a portion of the second enlarged peripheral surface is capable of contacting at least a portion of the periphery of the opening in the patient tissue, the second instrument holding portion of the second adapter being different than the instrument holding portion of the first adapter.

7. The adapter of claim 6, the adapter further including a third adapter, the third adapter having a third body having a third shim portion and a third instrument holding portion adjacent the third shim portion, wherein the third shim portion provides a third enlarged peripheral surface adjacent the suturing device such that when the suturing device is held in the third instrument holding portion and the suturing device and the third body are inserted through the opening in the patient tissue, at least a portion of the third enlarged peripheral surface is capable of contacting at least a portion of the periphery of the opening in the patient tissue, the third instrument holding portion of the third adapter being different than the instrument holding portion of the first adapter and the second instrument holding portion of the second adapter.

8. The adapter of claim 1, the instrument engaging feature being configured to resiliently hold the adapter to the suturing device.

9. The adapter of claim 1, further comprising a distal sheath removably attachable to the body.

10. The adapter of claim 9, wherein the adapter includes a connecting feature for detachably connecting the distal sheath to the body.

11. The adapter of claim 1, wherein the at least one instrument engaging feature comprises a protrusion.

12. A medical device comprising:
an elongated suturing device having a first surface that includes at least one adapter engaging feature; and
an adapter operatively associated with the elongated suturing device, the adapter comprising a body having a proximal end, a distal end, a shim portion, and an instrument holding portion adjacent the shim portion, the instrument holding portion having an inner surface and an opposing peripheral outer edge, the inner surface bounding a groove extending longitudinally along the body, the inner surface complementary to the first surface, the inner surface including at least one instrument engaging feature formed thereon and configured to receive the at least one adapter engaging feature, the engagement of the at least one adapter engaging feature and the at least one instrument engaging feature removably affixing the elongated suturing device to the adapter, the shim portion being configured to provide an enlarged peripheral surface adjacent the suturing device, and the instrument holding portion being shaped to hold a section of the suturing device, with another section of the suturing device protruding laterally away from the shim portion and beyond a first portion of the peripheral outer edge of the instrument holding portion, the first portion being located proximally of the distal end and distally of the proximal end and being laterally aligned with the at least one instrument engaging feature.

13. The medical device of claim 12, wherein the groove extends only partially along the length of the body such that the suturing device can be inserted laterally into the instrument holding portion through the groove.

14. The medical device of claim 13, wherein the suturing device includes an instrument mechanism and wherein the body defines an aperture positioned to be aligned with the instrument mechanism when the suturing device is held by the instrument holding portion, such that the instrument mechanism can extend through the aperture.

15. The medical device of claim 12, wherein the adapter is configured to be received on a left side of the suturing device.

16. The medical device of claim 12, wherein the adapter is configured to be received on a top side of the suturing device.

17. The medical device of claim 12, wherein the adapter is configured to be received on a right side of the suturing device.

18. The medical device of claim 12, wherein the shim portion comprises two shim portions, one disposed adjacent a proximal end and one disposed adjacent a distal end, and further including a reduced cross-sectional area disposed therebetween.

19. An adapter for a suturing device, the adapter comprising:
an elongated body having a proximal end and a distal end and a first surface that includes at least one adapter engaging feature;
an instrument holding portion defined along at least a portion of the length of the elongated body, the instrument holding portion having an inner surface and an opposing peripheral outer edge, the inner surface bounding a groove extending longitudinally along the elongated body, the inner surface being complementary to the first surface, the inner surface including at least one instrument engaging feature complementary to and capable of receiving the at least one adapter engaging feature, the engagement of the at least one adapter engaging feature and the at least one instrument engaging feature removably affixing a portion of a suturing device to at least a portion of the elongated body and allowing another portion of the suturing device adjacent to the instrument holding portion to protrude laterally beyond a first portion of the peripheral outer edge of the instrument holding portion, the first portion being located proximally of the distal end and distally of the proximal end, the first portion being laterally aligned with the first engagement feature; and
a shim portion along at least a portion of the length of the elongated body, the shim portion extending away from the instrument holding portion, the portion of the suturing device laterally extending beyond the first portion also laterally extending away from the shim portion.

20. The adapter of claim 19, further comprising a distal sheath that is detachable from the body.

21. The adapter of claim 20, wherein the adapter includes a connecting feature for detachably connecting the distal sheath to the body.

22. The adapter of claim 19, wherein the shim portion is adjacent a proximal end of the elongated body.

23. The adapter of claim 22, further including a second shim portion, the second shim portion adjacent a distal end of the elongated body.

* * * * *